(12) United States Patent  
Yasuda (10) Patent No.: US 8,134,713 B2
(45) Date of Patent: Mar. 13, 2012

(54) VARIABLE SPECTROSCOPY ELEMENT, SPECTROSCOPY APPARATUS, AND ENDOSCOPE SYSTEM

(75) Inventor: Tomoaki Yasuda, Tokyo (JP)

(73) Assignee: Olympus Corporation, Tokyo (JP)

( * ) Notice: Subject to any disclaimer, the term of this patent is extended or adjusted under 35 U.S.C. 154(b) by 392 days.

(21) Appl. No.: 12/526,712

(22) PCT Filed: Feb. 8, 2008

(86) PCT No.: PCT/JP2008/052128
§ 371 (c)(1),
(2), (4) Date: Aug. 11, 2009

(87) PCT Pub. No.: WO2008/099779
PCT Pub. Date: Aug. 21, 2008

(65) Prior Publication Data
US 2010/0022840 A1    Jan. 28, 2010

(30) Foreign Application Priority Data
Feb. 13, 2007  (JP) ................................. 2007-032248

(51) Int. Cl.
*G01J 3/45* (2006.01)
(52) U.S. Cl. ........................................ 356/454; 359/578
(58) Field of Classification Search .................. 356/454, 356/455, 480, 506; 359/578, 579
See application file for complete search history.

(56) References Cited

U.S. PATENT DOCUMENTS

| | | | | |
|---|---|---|---|---|
| 5,550,373 A | * | 8/1996 | Cole et al. ................. | 250/338.1 |
| 6,961,182 B2 | * | 11/2005 | Murata ........................ | 359/578 |

FOREIGN PATENT DOCUMENTS

| | | |
|---|---|---|
| JP | 64-041293 | 2/1989 |
| JP | 2002-277758 | 9/2002 |
| JP | 2006-303408 | 11/2006 |

* cited by examiner

*Primary Examiner* — Michael A Lyons
*Assistant Examiner* — Jonathan Hansen
(74) *Attorney, Agent, or Firm* — Scully, Scott, Murphy & Presser, P.C.

(57) ABSTRACT

Sensor electrodes and wiring patterns can be formed with fewer processes, and easy assembly without interference between the wires and optical substrates is realized. Provided is a variable spectroscopy element (1) that includes two optical substrates (3a, 3b) that oppose each other at a distance therebetween and that include reflection films (2) on the opposing surfaces; actuators (3c) that change the distance between the optical substrates; sensors (6) having electrode portions (6a, 6b) that detect the distance between the optical substrates on the opposing surfaces; inclined surfaces (5) that are provided on at least one of the optical substrates (3a (3b)), in the outer peripheral parts of the opposing surfaces, and gradually increase the distance from the other optical substrate (3b (3a)) radially outward and in the plate-thickness direction; and connecting patterns (6e, 6f) that are provided on the inclined surfaces (5) and connect wiring patterns (6c (6d)) that connect to the electrode portions (6a (6b)) of the sensor (6) and connecting patterns (6e, (6f)) that are disposed radially outward with respect to the wiring patterns (6c, (6d)) and connect to wires (7) that output signals from the electrode portions (6a, (6b)) to external parts.

6 Claims, 11 Drawing Sheets

VARIABLE SPECTROSCOPY ELEMENT, SPECTROSCOPY APPARATUS, AND ENDOSCOPE SYSTEM

TECHNICAL FIELD

The present invention relates to a variable spectroscopy element, a spectroscopy apparatus, and an endoscope system.

BACKGROUND ART

Etalon-type variable spectroscopy elements in which two optical substrates provided with optical coating layers on the opposing surfaces face each other and in which the distance therebetween is changeable have been known (for example, refer to Patent Document 1).

This variable spectroscopy element includes sensor electrodes of electrostatic capacitance sensors disposed on the opposing surfaces of the two optical substrates and is capable of detecting the distance between the optical substrates using the electrostatic capacitance sensor and controlling the distance therebetween while maintaining parallelism.

In the variable spectroscopy element in Patent Document 1, level differences are provided on outer peripheral parts of the optical substrates where the sensor electrodes, which connect wires, are provided in order to secure sufficient space for the wires that connect to the sensor electrodes to enable functioning of the electrostatic capacitance sensors; and the outer peripheral parts of the opposing optical substrates are cut away so that interference between the wires or between the wires and the optical substrates is avoided.

Patent Document 1: Japanese Unexamined Patent Application, Publication Number. 2002-277758.

DISCLOSURE OF INVENTION

In such a variable spectroscopy element in Patent Document 1, a coating formed by depositing metal such as aluminum on the surfaces of the optical substrates is known to be used as the sensor electrodes of the electrostatic capacitance sensors; however, when forming the sensor electrodes on optical substrates on which the level differences are formed, as in the variable spectroscopy element in Patent Document 1, there is a case a problem arises in that it is difficult to form a coating on the vertical surface of the level difference. Consequently, there is a case such as breakages formed in wiring patterns that connect to the sensor electrodes and an increase in electrical resistance occur. Improvement thereof requires deposition from two directions in two separate processes, leading to an inconvenience in that the manufacturing process becomes complicated.

In a structure where the optical substrates are provided with notches in the outer peripheral parts and in opposing positions of wires extending from the wiring patterns formed on the flat surfaces, there is a susceptibility to the wire breakages caused by interference between wires and parts other than the notches is possible when the two optical substrates are moved relative to each other in the circumferential direction. In particular, because the optical substrates in an extremely small variable spectroscopy element, such as those provided in the tip of an insertion portion of an endoscope, are themselves extremely small, it is difficult to initially match the phases between the wires connected to one optical substrate and the notches in the other optical substrate, thus leading to a drawback that wires break when the substrates interfere with the wires during assembly and the like.

The present invention provides a variable spectroscopy element, a spectroscopy apparatus, and an endoscope system, in which it is possible to form sensor electrodes and wiring patterns in fewer processes, thus enabling easy assembly without interference between the wires and the optical substrates.

A first aspect of the present invention provides a variable spectroscopy element including two optical substrates that oppose each other at a distance therebetween and that include reflection films on opposing surfaces; actuators that change the distance between the optical substrates; sensors having electrode portions that detect the distance between the optical substrates on the opposing surfaces; inclined surfaces that are provided on at least one of the optical substrates, in outer peripheral parts of the opposing surfaces, and that are disposed so as to gradually increase the distance from the other optical substrate radially outward and in the plate-thickness direction; wiring patterns that are provided on the inclined surfaces and connect to the electrode portions of the sensor; and connecting patterns that are disposed radially outward with respect to the wiring patterns and connect to wires that output signals from the electrode portions to the exterior.

In the above-described first aspect, the inclined surfaces may be provided on at least one of the optical substrates along the entire circumference.

In the above-described first aspect, both of the optical substrates may be provided with the above-described inclined surfaces.

In the above-described first aspect, at least a part of the inclined surfaces, in the circumferential direction, is provided with areas without wiring patterns and connecting patterns.

A second aspect of the present invention provides a spectroscopy apparatus including one of the above-described variable spectroscopy elements and an image-acquisition device that captures light spectrally separated by the variable spectroscopy element.

A third aspect of the present invention provides an endoscope system including the above-described spectroscopy apparatus.

According to the present invention, it is possible to form the sensor electrodes and the wiring patterns in fewer processes, and to realize easily assembly without interference between the wires and optical substrates.

EXPLANATION OF REFERENCE SIGNS 1 variable spectroscopy element
2 coating layer (reflection film)
3a, 3b optical substrate
3c actuator
5 inclined surface
6 sensor
6a, 6b sensor electrode (electrode portion)
6c, 6d wiring pattern
6e, 6f connecting pattern
7 wire
10 endoscope system
12 image-acquisition unit (spectroscopy apparatus)
20 image-acquisition device

BEST MODE FOR CARRYING OUT THE INVENTION

A variable spectroscopy element 1 according to an embodiment of the present invention will be described below with reference to FIG. 1, FIG. 2, and FIG. 11.

Figure 1:
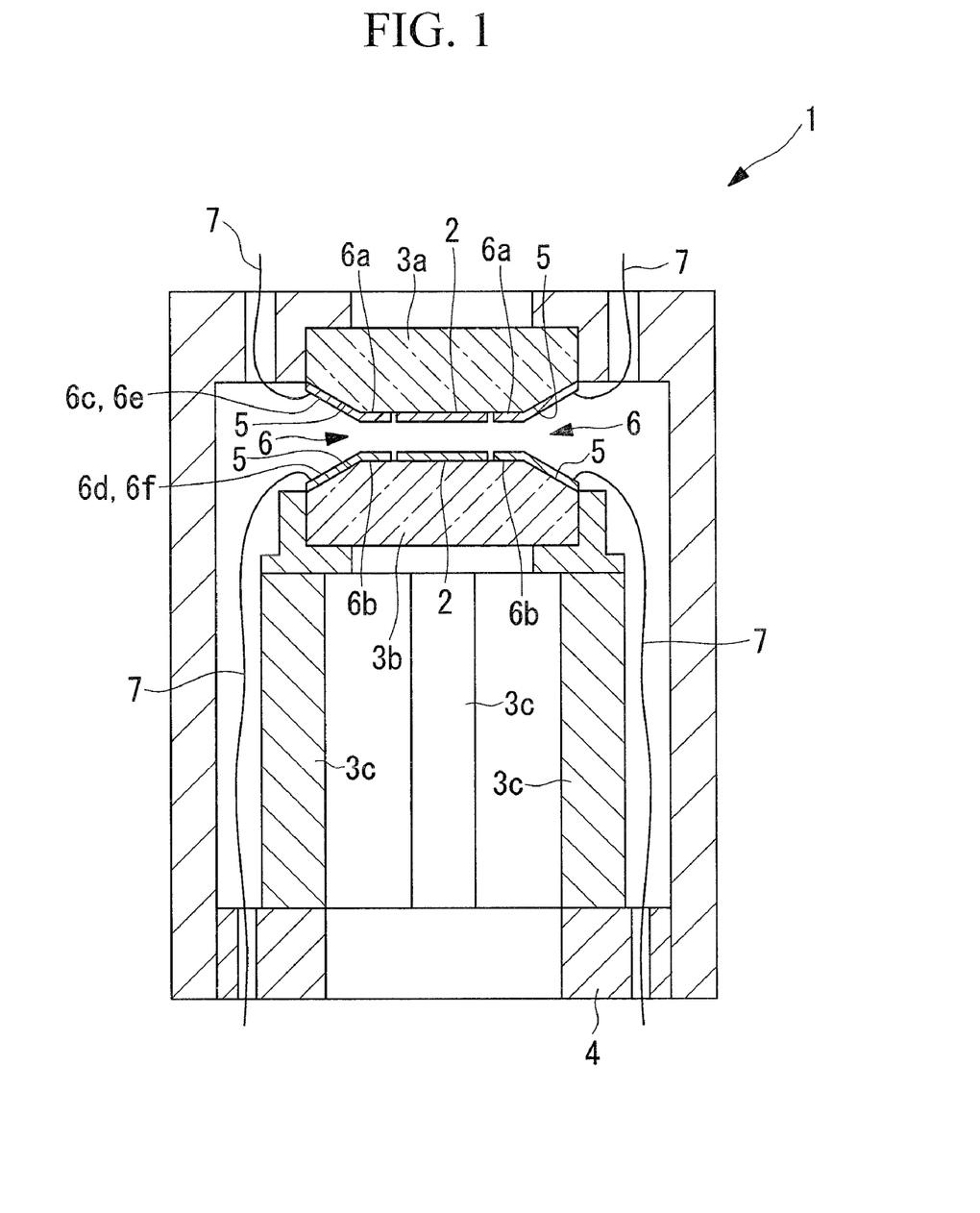
FIG. 1 is a longitudinal sectional view showing a variable spectroscopy element according to an embodiment of the present invention.

As shown in FIG. 1, the variable spectroscopy element 1 according to this embodiment is an etalon-type optical filter that includes, for example, two circular plate-like optical substrates 3a and 3b disposed in parallel with a gap therebetween and provided with reflection films (optical coating layers) 2 on the opposing surfaces; and actuators 3c for changing the distance between the optical substrates 3a and 3b. The optical substrate 3a is directly fixed on a frame member 4, and the optical substrate 3b is mounted to the frame member 4 with the actuators 3c interposed therebetween.

The two optical substrates 3a and 3b are provided with tapered inclined surfaces 5 formed around the entire circumference on the outer peripheral parts of the respective opposing surfaces. The inclined surfaces 5 are radially and outwardly sloping in the direction that gradually widens the distance between the two optical substrates 3a and 3b.

Figure 11:
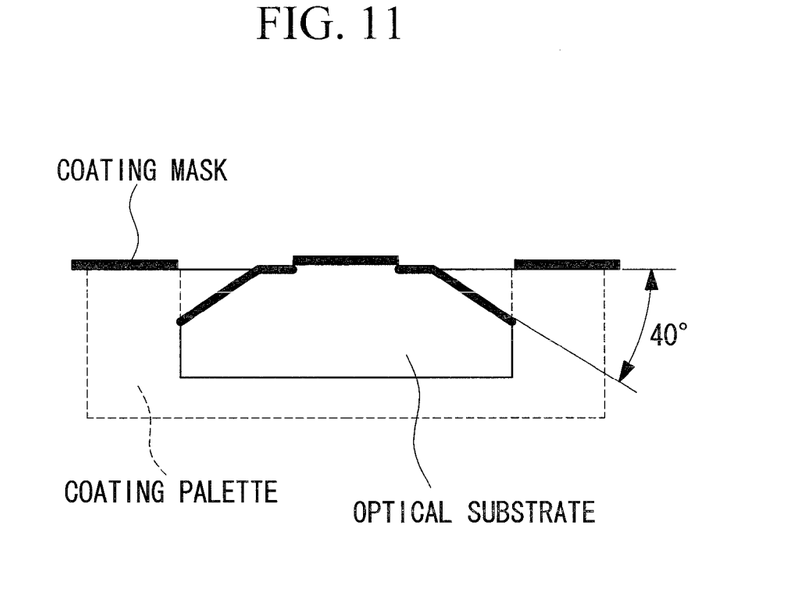
FIG. 11 is an explanatory diagram of manufacturing processes of the variable spectroscopy element shown in FIG. 1.

In the variable spectroscopy element 1 according to this embodiment, the tapered inclined surfaces 5 provided on the optical substrates 3a and 3b are manufactured at a tilt angle $\alpha=40°$, as shown in FIG. 11.

The actuators 3c are multilayer piezoelectric elements and are disposed at four locations in the circumferential direction along the circumferential edge of the optical substrate 3b with equal distances therebetween.

This variable spectroscopy element 1 changes the distance between the optical substrates 3a and 3b by the action of the actuators 3c, thereby making it possible to change the wavelength band of light transmitted in the axial direction.

The two optical substrates 3a and 3b include sensors 6 for detecting the distance between the optical substrates 3a and 3b. The sensors 6 are of the electrostatic capacitance type, are provided on peripheral parts of the optical substrates 3a and 3b outside an optically effective diameter B (refer to FIG. 2), and include four pairs of sensor electrodes 6a and 6b.

Figure 2:
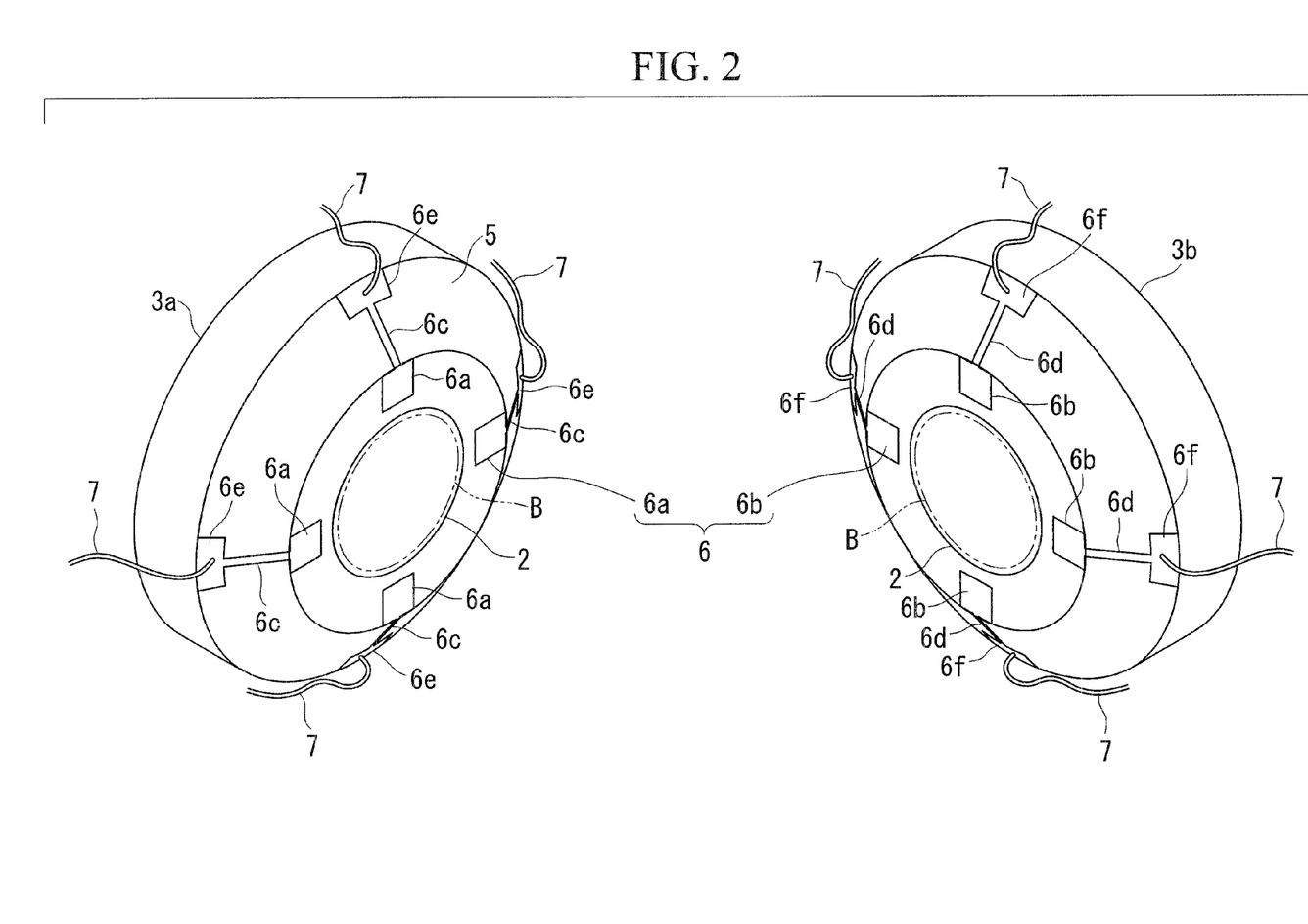
FIG. 2 is a perspective view showing a pair of optical substrates provided in the variable spectroscopy element shown in FIG. 1.

These sensor electrodes 6a and 6b are, as shown in FIG. 2, disposed in the peripheral parts of the optical substrate 3a with equal distances therebetween in the circumferential direction, and at mutually opposing positions. In addition, the respective sensor electrodes 6a and 6b are provided with wiring patterns 6c and 6d that connect to the sensor electrodes 6a and 6b, and wiring pads (connecting patterns) 6e and 6f that connect to the wiring patterns 6c and 6d. The sensor electrodes 6a and 6b, the wiring patterns 6c and 6d, and the wiring pads 6e and 6f are integrally coated on the surfaces of the optical substrates 3a and 3b by depositing a material such as aluminum.

In this embodiment, the wiring patterns 6c and 6d and the wiring pads 6e and 6f are disposed on the inclined surfaces 5, respectively. The wiring pads 6e and 6f are disposed farther outward in the radial direction than the wiring patterns 6c and 6d. In this way, the wiring pads 6e and 6f are disposed at positions separated by sufficient distances in the gap direction of the optical substrates 3a and 3b.

The wiring pads 6e and 6f have sufficiently large areas compared with the wiring patterns 6c and 6d so as to connect to wires 7 by, for example, wire bonding. In addition, the wiring patterns 6c (6d) are formed thinly enough not to form a large electrostatic capacitance between themselves and the opposing wiring patterns 6d (6c), and with a thickness not to act as a resistance to signal transfer from the sensor electrodes 6a and 6b.

Figure 12:
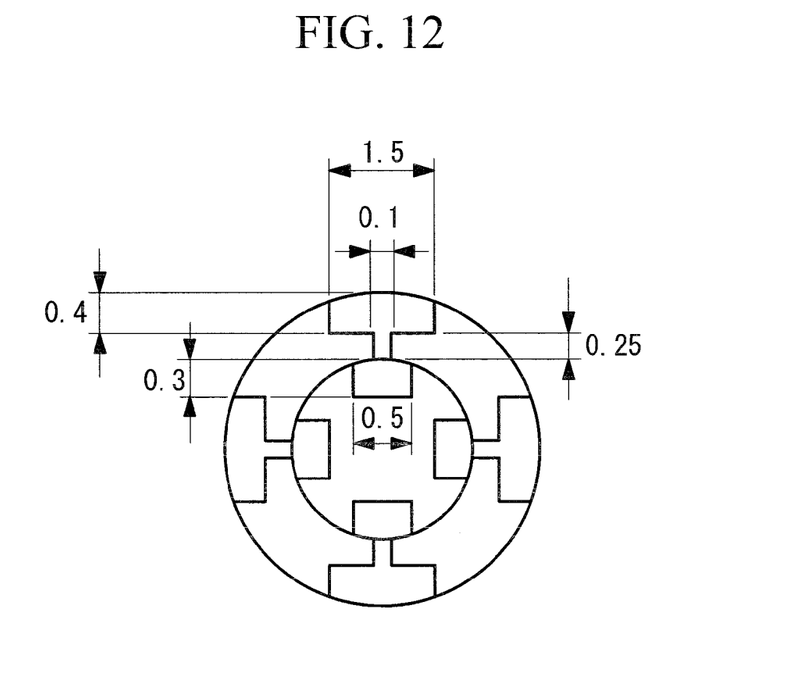
FIG. 12 is a diagram showing dimensions of individual parts of the variable spectroscopy element in FIG. 1.

In the variable spectroscopy element 1 according to this embodiment, respective parts are manufactured in the sizes shown below (refer to FIG. 12).

Sensor electrodes 6a, 6b: dimensions: 0.5×0.3 mm, thickness: 400 nm

Wiring patterns 6c, 6d: dimensions: 0.1×0.25 mm, thickness: 200 nm

Wiring pads 6e, 6f: dimensions: 1.5×0.4 mm, thickness: 200 nm

With these conditions, by manufacturing the tapered inclined surfaces 5 of the optical substrates 3a and 3b at the angle $\alpha=40°$, as described above, coating of the flat parts at a film thickness of approximately 400 nm, and that of the tapered parts at a film thickness of approximately 200 nm and above, are realized with a single coating process; and it is possible to manufacture the variable spectroscopy element 1 provided with sensors that achieve the advantages of the present invention. In addition, because the flat part and the tapered part form an obtuse angle of 130° therebetween, wire breakages at the borders are less likely to occur.

In fluorescence observation, in general, the obtained fluorescence intensity is weak, and thus the transmission efficiency of an optical system is of extreme importance. In the etalon-type variable spectroscopy element 1, a high transmittance is obtained when the reflection films are parallel; however, the transmittance abruptly declines when there are errors in adjusting the parallelism. Accordingly, as an image-acquisition unit for fluorescence observation, it is desirable to include a plurality of the sensors 6 and a plurality of the actuators 3c in order to correct inclination errors of the two optical substrates 3a and 3b when the distance therebetween is changed.

By carrying out feedback control of drive signals to the actuators 3c based on signals from the sensor electrodes 6a and 6b, it is possible to improve the precision of the control of the transmittance characteristics.

The operation of the thus-configured variable spectroscopy element 1 according to this embodiment will be described below.

In the variable spectroscopy element 1 according to this embodiment, by allowing light entry into the areas of the optically effective diameter B of the two parallel-spaced optical substrates 3a and 3b, only the light with a wavelength determined by the distance between the optical substrates 3a and 3b is transmitted through the two optical substrates 3a and 3b, whereas the remaining light is reflected. Then, the wavelength of light transmitted through the two optical substrates 3a and 3b is changed by changing the distance between the two optical substrates 3a and 3b by the action of the actuators 3c, and thus light in a desired wavelength band can be spectrally separated from light in other wavelength bands.

Because the sensor electrodes 6a and 6b are disposed opposing each other on the opposing surfaces of the optical substrates 3a and 3b, voltage signals that indicate the electrostatic capacitance formed between the sensor electrodes 6a and 6b can be detected, and it is possible to detect the distance between the sensor electrodes 6a and 6b based on the voltage signals. Because four pairs of the sensor electrodes 6a and 6b are provided on the optical substrates 3a and 3b in the circumferential direction with spaces therebetween, the distance between the optical substrates 3a and 3b at the corresponding positions can be detected by the respective pairs of the sensor electrodes 6a and 6b, and the distance can be precisely adjusted while maintaining the parallelism between the two optical substrates 3a and 3b, by controlling the actuators 3c based on the detected distance.

Here, the variable spectroscopy element 1 according to this embodiment is provided with the tapered inclined surfaces 5 on the outer peripheral parts of the optical substrates 3a and 3b and the wiring patterns 6c and 6d and the wiring pads 6e and 6f are formed on the inclined surfaces 5, thus providing a sufficiently large distance therebetween at the positions of the wiring pads 6e and 6f; therefore, the electrostatic capacitance formed between the opposing wiring pads 6e and 6f can be sufficiently suppressed. In addition, as for the wiring patterns 6c and 6d, although mutually adjacent parts exist, because their width is formed sufficiently small, the electrostatic capacitance formed can be suppressed in a similar manner.

Furthermore, by providing the wiring patterns 6c and 6d and the wiring pads 6e and 6f on the inclined surfaces 5 bordering the opposing surfaces of the optical substrates 3a and 3b, it is possible to integrally manufacture the sensor electrodes 6a and 6b, the wiring patterns 6c and 6d, and the wirings pads 6e and 6f by a single manufacturing process by means of aluminum deposition from one direction. In this case, in comparison to a conventional type, in which deposition on the vertical surfaces of the level differences is difficult, deposition can be simplified, and a coating with a stable thickness can be formed. As a result, signals from the sensor electrodes 6a and 6b can be precisely output to external parts, without the occurrence of wire breakage and increases in the electrical resistance.

In the variable spectroscopy element 1 according to this embodiment, the wiring pads 6e and 6f that connect to the wires 7 are disposed on the outermost peripheral positions of the inclined surfaces 5 of the optical substrates 3a and 3b; thus, it is possible to secure a sufficiently large distance between the wiring pads 6e and 6f, even if the optical substrates 3a and 3b are brought sufficiently close to each other. Therefore, the wires 7 connected to the wiring pads 6e and 6f can be prevented from interfering with each other.

Specifically, because the inclined surfaces 5 are formed around the entire circumference of both optical substrates 3a and 3b, interference does not occur between the wires 7 and the optical substrates 3a and 3b, even if the optical substrates 3a and 3b are relatively moved in the circumferential direction with respect to each other. Consequently, damage to the wires 7 due to interference with the optical substrates 3a and 3b and other wires 7 can be prevented, even if the phases between the optical substrates 3a and 3b are adjusted during assembly, etc., so as to dispose the sensor electrodes 6a and 6b in mutually opposing positions.

The inclined surfaces 5 adopted in the variable spectroscopy element 1 according to this embodiment are formed as tapered surfaces with a single slope angle; alternatively, however, inclined surfaces 5 with a curved surface form, where the slope angle gradually changes, may be adopted.

Figure 3:
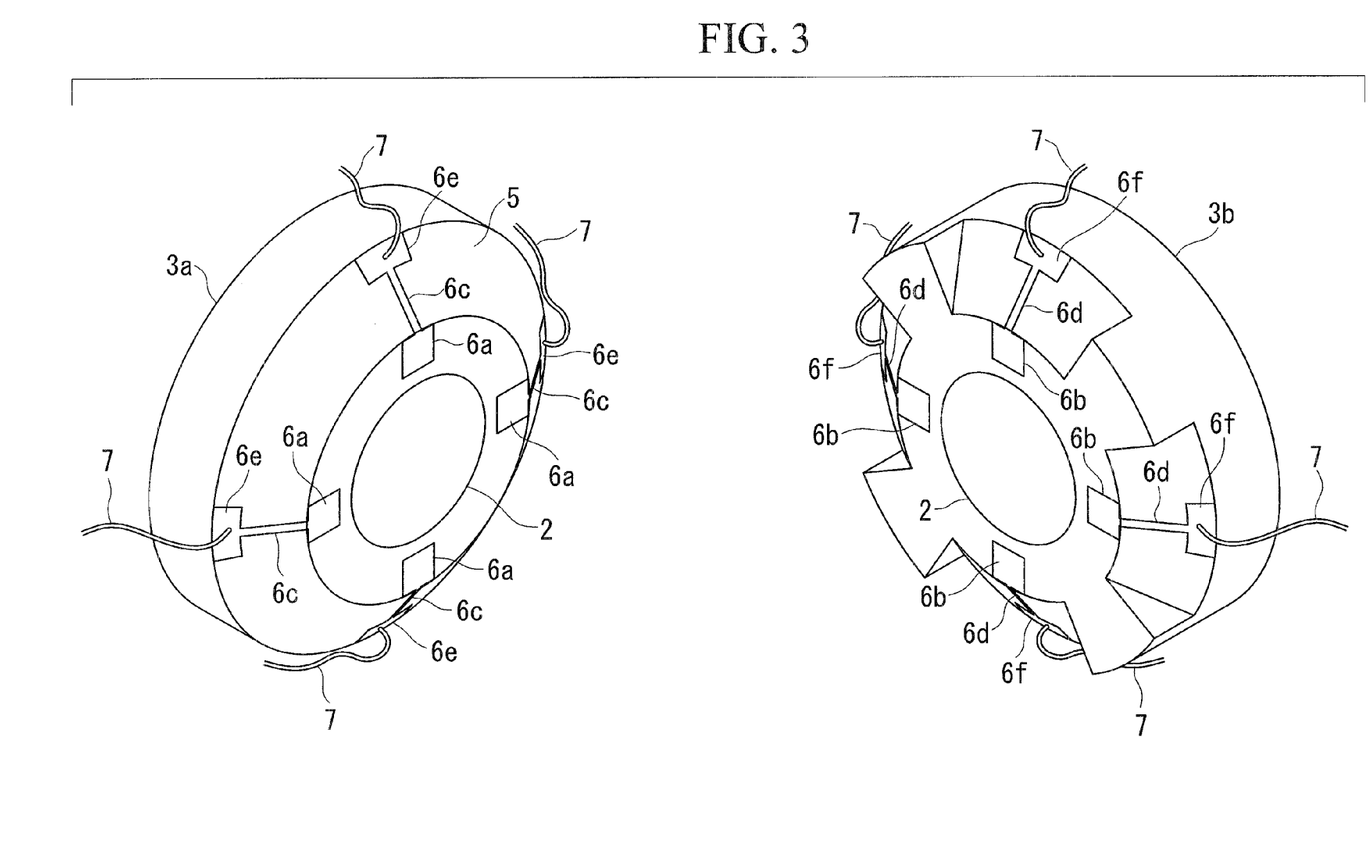
FIG. 3 is a perspective view showing a modification of the optical substrates shown in FIG. 2.

In the variable spectroscopy element 1 according to this embodiment, the two optical substrates 3a and 3b are both provided with the inclined surfaces 5 formed on the outer peripheral parts along the entire circumference; alternatively, however, as shown in FIG. 3, one optical substrate 3b may be provided partially with the inclined surfaces 5 on the parts where the wiring pads 6f are formed. In this case, as for the other optical substrate 3a, it is preferable to provide the inclined surfaces 5 along the entire circumference. The optical substrates 3a and 3b may be exchanged. Additionally, both of the optical substrates 3a and 3b may be provided with partial inclined surfaces 5.

It is not necessarily required that the wiring pads 6e and 6f be disposed on the inclined surfaces 5, as long as the wiring patterns 6c and 6d, which connect the sensor electrodes 6a and 6b and the wiring pads 6e and 6f, are disposed on the inclined surfaces 5.

Although the sensor electrodes 6a and 6b are disposed at four locations in the circumferential direction of the optical substrates 3a and 3b with spaces therebetween, alternatively, they can be disposed at any number of locations equal to or greater than three. By having them at three or more locations, the flat surfaces of the optical substrates 3a and 3b can be established, thereby making it possible to achieve parallelism between the two optical substrates 3a and 3b with ease and precision.

Figure 4:
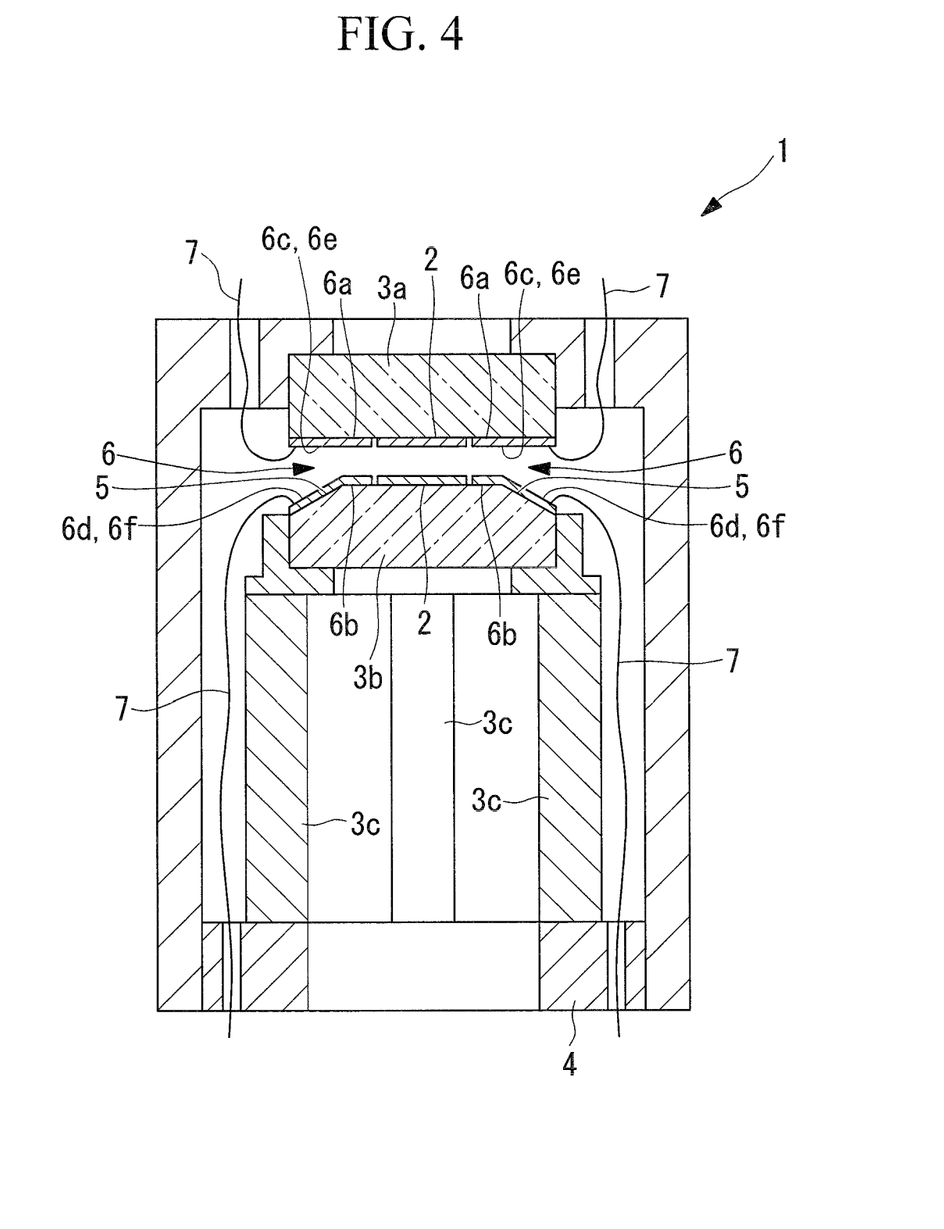
FIG. 4 is a longitudinal sectional view showing a modification of the variable spectroscopy element shown in FIG. 1.
Figure 5:
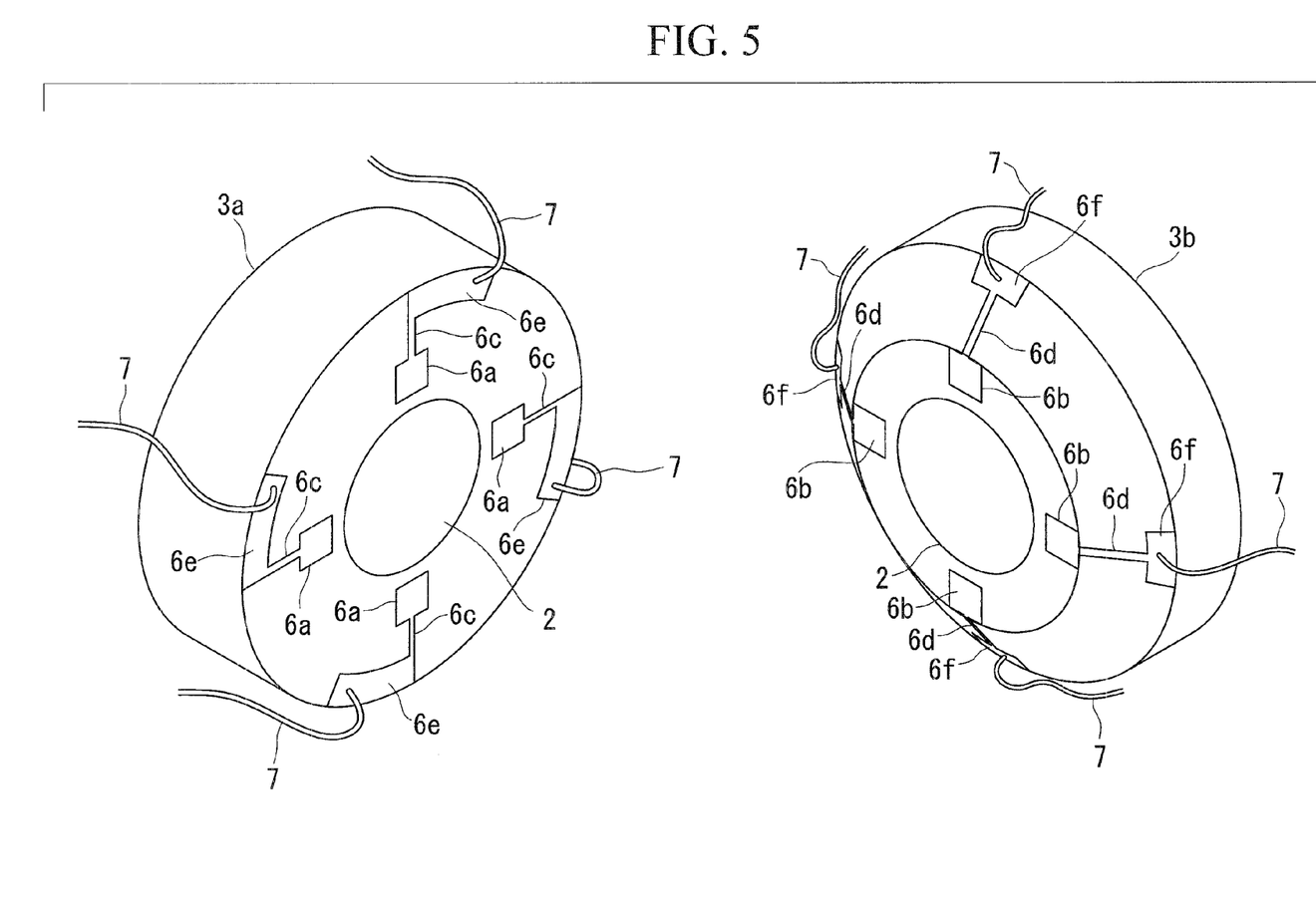
FIG. 5 is a perspective view showing the pair of optical substrates provided in the variable spectroscopy element shown in FIG. 4.
Figure 6:
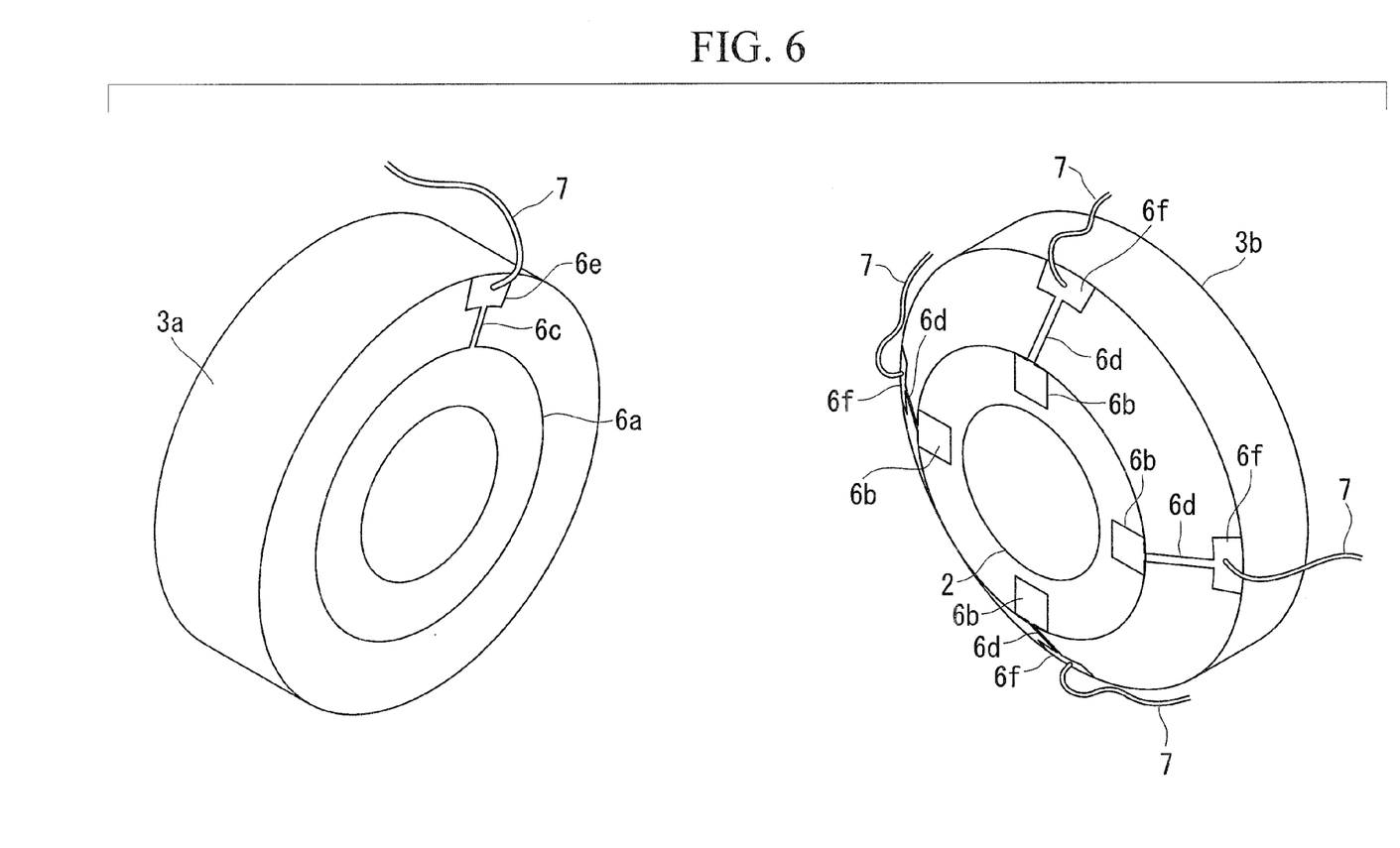
FIG. 6 is a perspective view showing a modification of the optical substrates shown in FIG. 5

As shown in FIG. 4 through FIG. 6, in the case where the inclined surfaces 5 are provided around the entire circumference of one optical substrate 3b, the inclined surfaces 5 need not be provided on the other optical substrate 3a. By doing so, the manufacturing can be further simplified because the other optical substrate 3a can be left flat. Note that the optical substrates 3a and 3b can be exchanged.

In this case, only the sensor electrodes 6a and 6b need to be disposed at opposing positions; as for the wiring patterns 6c and 6d and the wiring pads 6e and 6f, it is preferable that they are not opposing each other. Specifically, with respect to the wiring pads 6e and 6f, in order to avoid interference among the wires 7 connected thereto, it is preferable to dispose them with shifted phase, as shown in FIG. 5.

Furthermore, as shown in FIG. 6, as the sensor electrode 6a provided on one optical substrate 3a, a single sensor electrode 6a with a size and shape such that it opposes all sensor electrodes 6b provided on the other optical substrate 3b may be adopted. In this case, assembly can be carried out without consideration for deviation in the circumferential direction between the optical substrates 3a and 3b relative to each other; thus an even easier assembly operation is enabled, along with prevention of crosstalk noise and parasitic capacitance by keeping the wires 7 far from each other.

Even if the number of opposing sensor electrodes 6a and 6b differ, one sensor electrode 6a may be a shared electrode for the four sensor electrodes 6b provided on the optical substrate 3b. Therefore, as in the case where four sensor electrodes 6a are provided, it can function as four-pole sensors 6; thus, it is possible to detect four voltage signals, the same as the number of degrees of freedom for driving, in other words, the number of actuators 3c.

Therefore, light in a desired wavelength band can be spectrally separated with high precision by precisely controlling the distance between the two optical substrates 3a and 3b based on voltage signals that are equal in number to the number of the actuators 3c and that indicate the electrostatic capacitance corresponding uniquely to the distance between the two optical substrates 3a and 3b.

Furthermore, in this case, for example, in FIG. 4, the number of the wires 7 that move during the driving of the actuators 3c is reduced by reducing the number of the sensor electrodes 6b provided on the optical substrate 3b that changes its position by driving of the actuators 3c, relative to the number of the sensor electrodes 6a provided on the optical substrate 3a that is directly fixed on the frame member 4; thereby, the occurrence of noise due to changes in the capacitance among the wires 7 can be reduced.

Additionally, in the variable spectroscopy element 1 according to this embodiment, sensors of the electrostatic capacitance type are adopted as the sensors 6 for detecting the distance between the optical substrates 3a and 3b, and the sensor electrodes 6a and 6b are provided on the outer peripheral parts of the optical substrates 3a and 3b; alternatively, however, sensors of the eddy current type may be adopted, and sensor coils 6a and 6 may be provided on the outer peripheral parts of the optical substrates 3a and 3b.

Further, the reflection films 2 disposed on the opposing surfaces of the optical substrates 3a and 3b may be formed from electrically conductive materials, thus using the reflection films 2 themselves also as the sensor electrodes 6a and 6b for forming the electrostatic capacitance.

Figure 7:
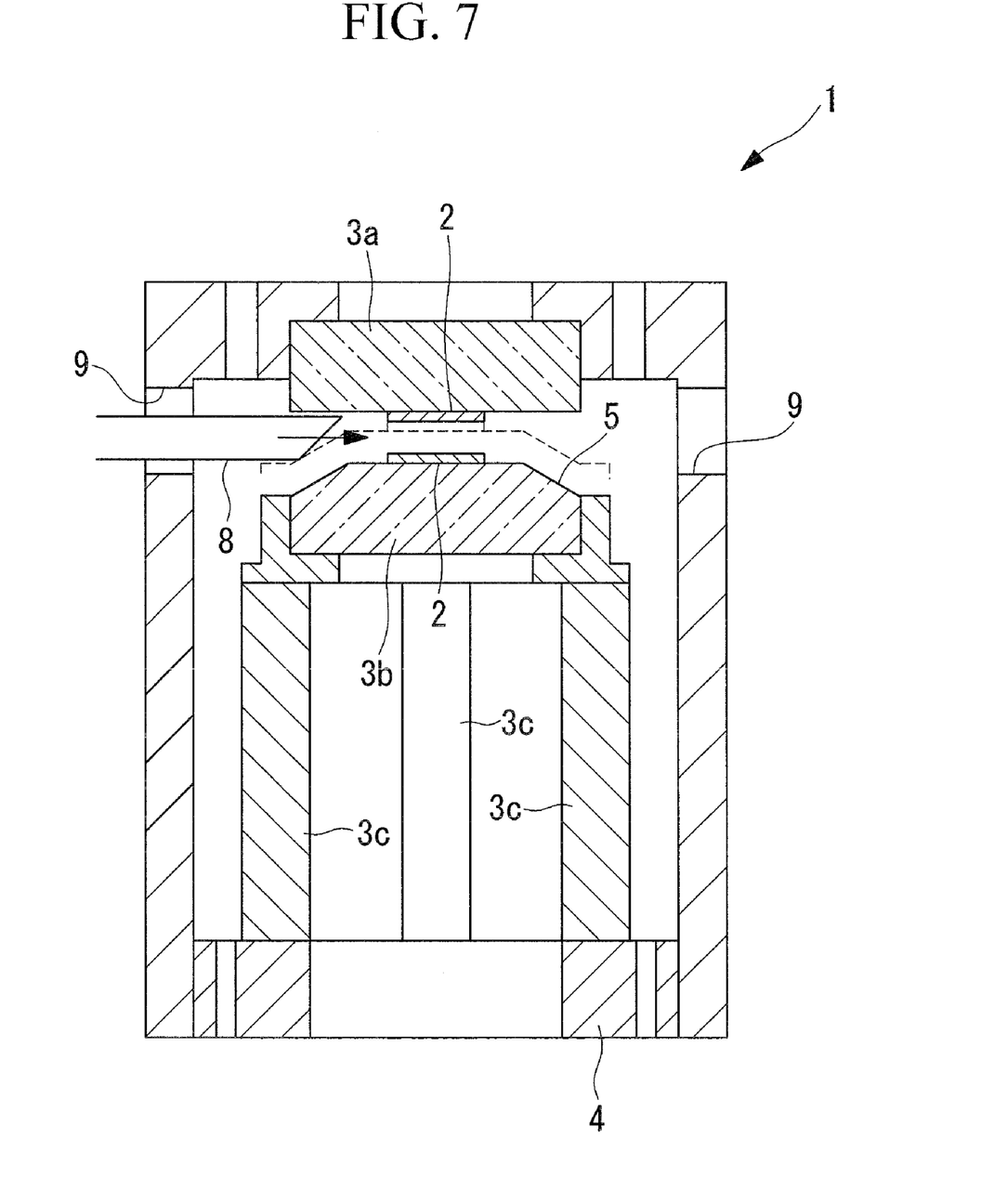
FIG. 7 is a longitudinal sectional view showing another modification of the variable spectroscopy element shown in FIG. 1.

In such a variable spectroscopy element as in this embodiment, to function as a spectroscope, the distance between the opposing surfaces of the optical substrates is extremely narrow, and the opposing surfaces of the respective optical substrates have a high surface precision. Therefore, during its assembly and operation, so-called optical contact, where the coating layers formed on the opposing surfaces of the optical substrates come in contact and become adhered to each other, can occur. Once in this state, because the stroke of an ordinary piezoelectric element is extremely small, its electrical stroke alone cannot resolve the above-described state. In the variable spectroscopy element 1 according to this embodiment, areas in which the wiring patterns 6c and 6d and the wiring pads 6e and 6f are not formed are provided on the inclined surfaces 5 of the optical substrates 3a and 3b. Thus, as shown in FIG. 7, the adhered-state can be easily resolved, separating the two, by inserting wedge-shaped jigs 8 in the radial direction in the areas without the wiring patterns 6c and 6d. Furthermore, because the wiring patterns 6c and 6d are not provided there, inserting the jigs 8 will not damage the wiring patterns 6c and 6d. In this case, the frame member 4 is provided with openings 9 that penetrate in the radial direction, as shown in FIG. 7.

Next, an endoscope system 10 according to an embodiment of the present invention will be described with reference to FIG. 8 to FIG. 10.

Figure 8:
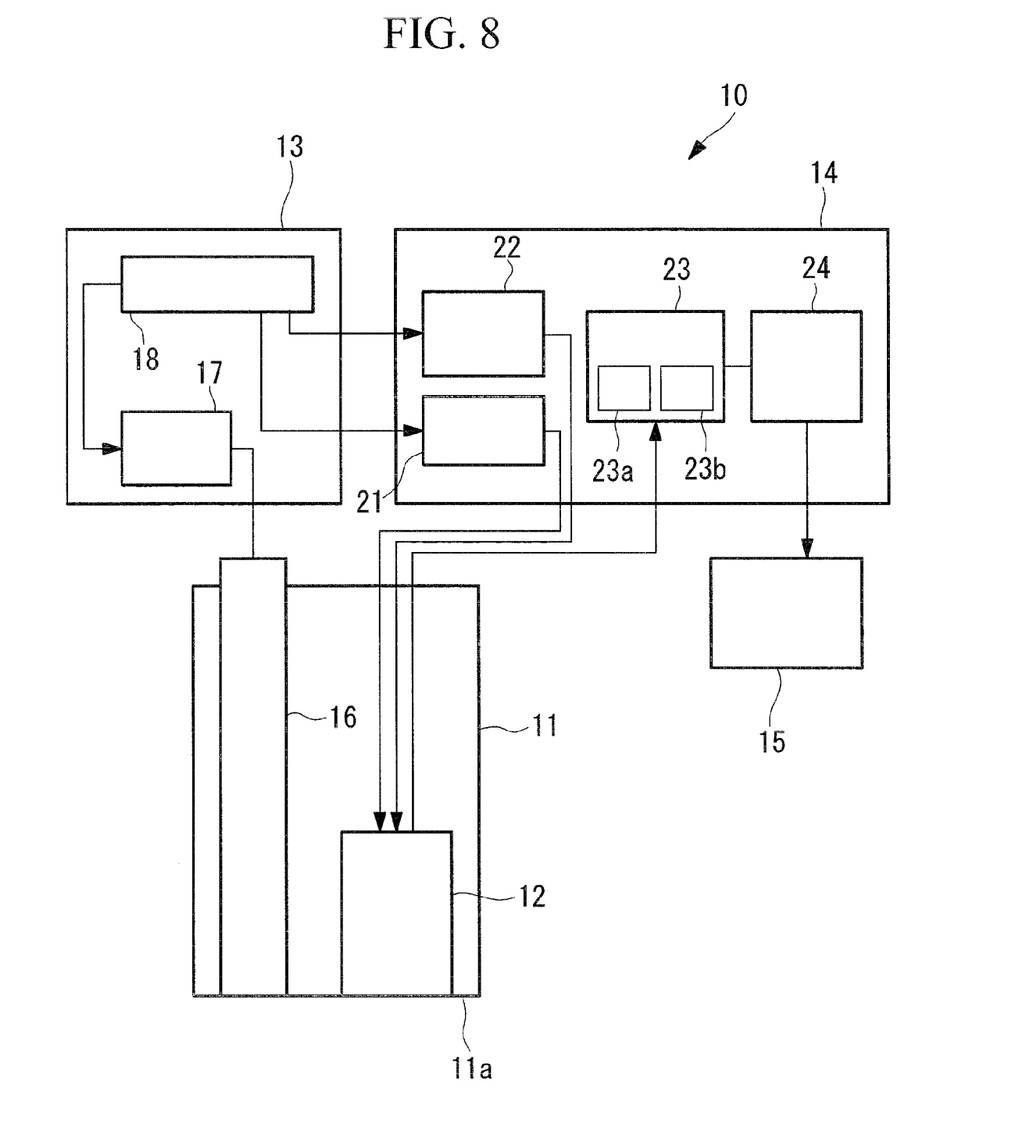
FIG. 8 is an overall configuration diagram showing an endoscope system according to an embodiment of the present invention.

The endoscope system 10 according to this embodiment, as shown in FIG. 8, includes an insertion portion 11 to be inserted into the body cavity of a living organism, an image-acquisition unit (spectroscopy apparatus) 12 disposed inside the insertion portion 11, a light source unit 13 that emits multiple types of light, a control unit 14 that controls the image-acquisition unit 12 and the light source unit 13, and a display unit 15 that displays images acquired by the image-acquisition unit 12.

The insertion portion 11 has extremely thin external dimensions allowing it to be inserted into the body cavity of a living organism and is provided, in the interior thereof, with the image-acquisition unit 12 and a light guide 16 that conveys light from the light source unit 13 to a distal end 11a.

The light source unit 13 is provided with an illumination light source 17 that generates illumination light for illuminating an observation target A in the body cavity and for obtaining reflected light that is reflected at and returns from the observation target A; and a light source control circuit 18 that controls the illumination light source 17.

The illumination light source 17 is, for example, a combination of a xenon lamp and a bandpass filter (not shown in the drawings), and the 50% transmission band of the bandpass filter is between 430 nm and 700 nm inclusive. In other words, the illumination light source 17 produces illumination light in a wavelength band between 430 nm and 700 nm inclusive.

Figure 9:
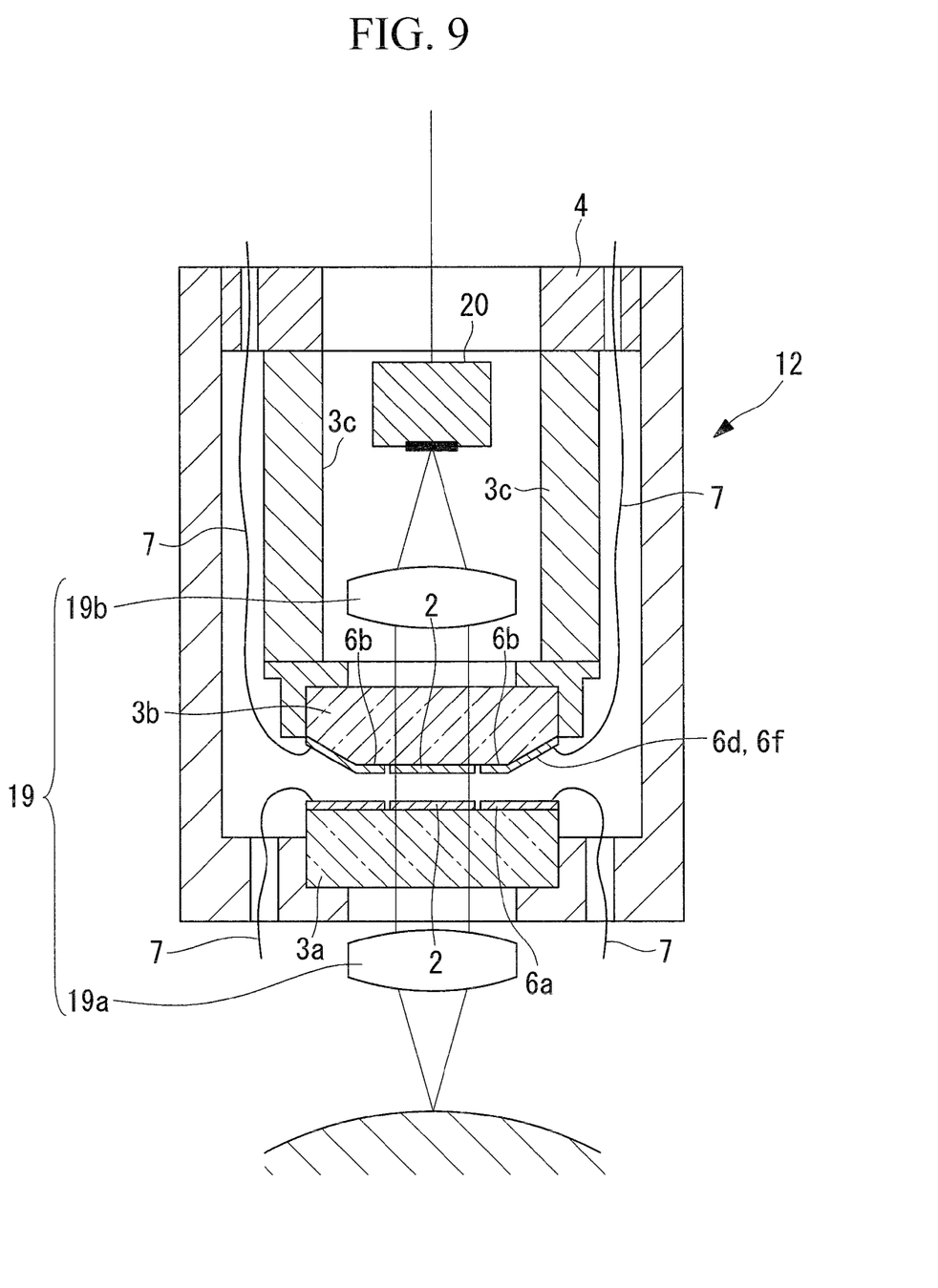
FIG. 9 is a longitudinal sectional view showing an image-acquisition unit provided in the endoscope system shown in FIG. 8.

As shown in FIG. 9, the image-acquisition unit 12 is disposed at the end of the insertion portion 11 and is provided with an image-acquisition optical system 19 including a first lens 19a and a second lens 19b for collecting incident light from the observation target A; the variable spectroscopy element 1 that is capable of changing the spectroscopy characteristics by the action of the control unit 14; and an image-acquisition device 20 that captures light collected by the image-acquisition optical system 19 and converts it to electrical signals.

Figure 10:
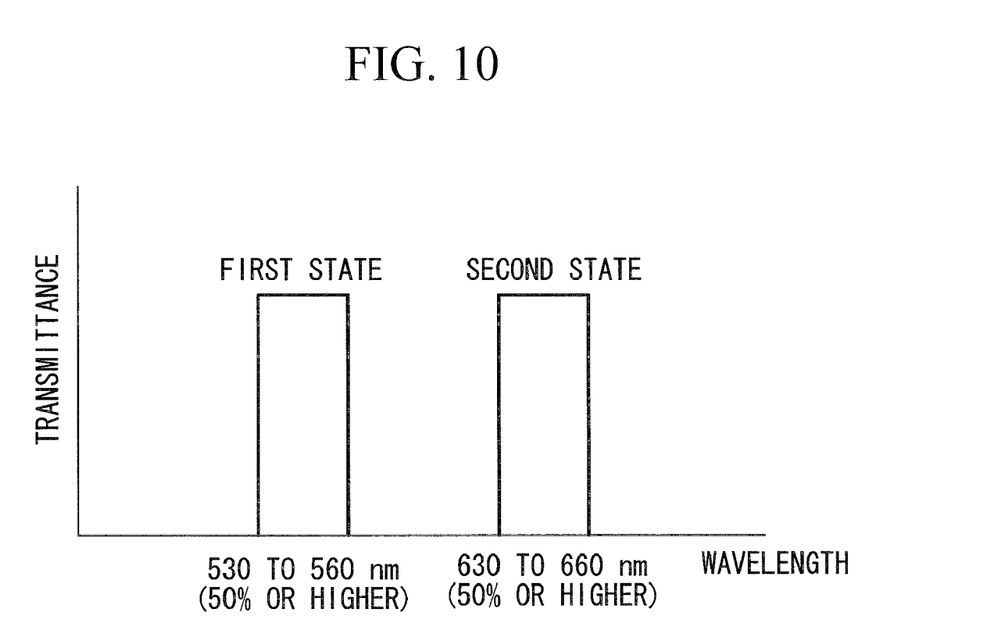
FIG. 10 is a diagram showing transmittance characteristics of a variable spectroscopy element constituting the image-acquisition unit shown in FIG. 9.

As shown in FIG. 10, the variable spectroscopy element 1 changes into two states depending on the control signals from the control unit 14.

The first state allows passage of light in the wavelength band between 530 nm and 560 nm inclusive, which is the green band of visible light (the transmission wavelength band is defined as wavelengths with a 50% transmittance).

The second state allows passage of light in the wavelength band between 630 nm and 660 nm inclusive, which is the red band of visible light.

As shown in FIG. 8, the control unit 14 is provided with an image-acquisition-device drive circuit 21 that performs drive control of the image-acquisition device 20; a variable-spectroscopy-element control circuit 22 that performs drive control of the variable spectroscopy element 1; a frame memory 23 that stores the image information obtained by the image-acquisition device 20; and an image processing circuit 24 that processes the image information stored in the frame memory 23 and outputs it to the display unit 15.

The image-acquisition-device drive circuit 21 and the variable-spectroscopy-element control circuit 22 are connected to the light source control circuit 18 and perform drive control of the variable spectroscopy element 1 and the image-acquisition device 20 in synchronization with the operation of the illumination-light light source 17 by the light source circuit 18.

More specifically, when the variable-spectroscopy-element control circuit 22 sets the variable spectroscopy element 1 to the first state, the image-acquisition-device drive circuit 21 outputs the image information output from the image-acquisition device 20 to a first frame memory 23a. In addition, when the variable-spectroscopy-element control circuit 22 sets the variable spectroscopy element 1 to the second state, the image-acquisition-device drive circuit 21 outputs the image information that is output from the image-acquisition device 20 to a frame memory 23b.

Furthermore, the image processing circuit 24 receives, for example, reflected-light image information in the green band from the first frame memory 23a, then outputs it on a first channel of the display unit 15. Additionally, the image processing circuit 24 receives reflected-light image information in the red band from the second frame memory 23b, then outputs it on a second channel of the display unit 15.

The operation of the thus-configured endoscope system 10 according to this embodiment is described below. To acquire images of an image-acquisition target A inside the body cavity of a living organism using the endoscope system 10 according to this embodiment, the insertion portion 11 is inserted into the body cavity, and its distal end 11a is positioned facing the image-acquisition target A inside the body cavity. In this state, the light source unit 13 and the control unit 14 are operated, activating the light source control circuit 18, thereby making the illumination-light light source 17 generate illumination light.

The illumination light generated in the light source unit 13 is conveyed to the distal end 11a of the insertion portion 11 via the light guide 16, and is radiated toward the image-acquisition target A from the distal end 11a of the insertion portion 11.

The illumination light is reflected at the surface of the image-acquisition target A and, after being converted to a substantially collimated beam by the first lens 19a, enters the variable spectroscopy element 1. Then, the reflected light transmitted through the variable spectroscopy element 1 is imaged on an image-acquisition surface of the image-acquisition device 20 by the second lens 19b, and reflected-light image information is obtained.

In this case, to obtain a reflected-light image in the green band, the wavelength band of the reflected light that reaches the image-acquisition device 20 is restricted to between 530 nm and 560 nm inclusive by activating the variable-spectroscopy-element control circuit 22 to switch the variable spectroscopy element 1 to the first state. The reflected-light image information obtained thereby is stored in the first frame memory 23a, is output on the first channel of the display unit 15, and is displayed thereon.

To obtain a reflected-light image in the red band, the wavelength band of the reflected light that reaches the image-acquisition device 20 is restricted to between 630 nm and 660 nm inclusive by activating the variable-spectroscopy-element control circuit 22 to switch the variable spectroscopy element 1 to the second state. The reflected-light image information obtained thereby is stored in the second frame memory 23b, is output on the second channel of the display unit 15, and is displayed thereon.

In this way, the endoscope system 10 according to this embodiment is capable of providing a user with image information with respect to different wavelength bands of the reflected light.

In this case, in the endoscope system 10 according to this embodiment, because the sensors 6 are provided in the variable spectroscopy element 1, the distance between the two optical substrates 3a and 3b is detected by the sensors 6 when switching to the first state and to the second state, and the voltage signals applied to the actuators 3c are feedback controlled. Accordingly, the diameter of the distal end 11a of the insertion portion 11 can be reduced; despite its small size, the distance between the optical substrates 3a and 3b is precisely controlled, light in the desired wavelength bands is spectrally separated with high precision, and thus it is possible to obtain clear fluorescence images and reflected-light images.

Furthermore, in this embodiment, because the inclined surfaces 5 are provided on the outer peripheral parts of the optical substrates 3a and 3b, and because the wiring patterns 6c and 6d, which connect to the sensor electrodes 6a and 6b, and the wiring pads 6e and 6f are provided on the inclined surfaces 5, the wiring pads 6e and 6f provided on the opposing optical substrates 3a and 3b are sufficiently distant, and thus the optical substrates 3a and 3b can be brought sufficiently close together without causing the wires 7 that are connected to the wiring pads 6e and 6f to interfere with each other.

Hence, the occurrence of crosstalk noise can be reduced by preventing the wires 7 from approaching each other.

Note that, any one of the elements shown in FIG. 1 through FIG. 7 may be adopted as the variable spectroscopy element 1 for the endoscope system 10 according to this embodiment.

In addition, although the second lens 19b and the image-acquisition device 20 are disposed at the inner side of the actuators, it is not limited to this.

Further, any type of device may be adopted as the image-acquisition device 20, such as C-MOS, a photodiode, an electron multiplier CCD (EMCCD), and an electron bombardment CCD (EBCCD).

Additionally, magnetostrictive elements may be used as the actuators, instead of the piezoelectric elements.

In addition, although a system for obtaining reflected-light images was described for the endoscope system 10 according to this embodiment, instead, it can be used for other observation methods such as obtaining fluorescence images and reflected-light images.

Further, this embodiment may be applied not only to flexible scopes with bending sections but also to rigid scopes. Additionally, the observation target A is not limited to living organisms. It may be applied to industrial endoscopes which target the insides of pipes, machinery, and structures.

In addition, although the endoscope system 10 wherein the variable spectroscopy element 1 is provided in the image-acquisition unit 12 is described in this embodiment, alternatively, it may be an endoscope system wherein the variable spectroscopy element 1 is provided in a light source unit disposed at the end of the insertion portion 11.

The invention claimed is:

1. A variable spectroscopy element comprising:
   two optical substrates that oppose each other at a distance there between and that include reflection films on opposing surfaces; and
   actuators that change the distance between the optical substrates;
   sensors having electrode portions that detect the distance between the optical substrates on the opposing surfaces; and
   inclined surfaces that are provided on at least one of the optical substrates, in outer peripheral parts of the opposing surfaces, and that are disposed so as to gradually increase the distance from the other optical substrate radially outward and in the plate-thickness direction;
   wiring patterns that are provided on the inclined surfaces and connect to the electrode portions of the sensors; and
   connecting patterns that are disposed radially outward with respect to the wiring patterns and connect to wires that output signals from the electrode portions to external parts.

2. A variable spectroscopy element according to claim 1, wherein the inclined surfaces on at least one of the optical substrates are provided around the entire circumference.

3. A variable spectroscopy element according to claim 1, wherein both of the optical substrates are provided with the inclined surfaces.

4. A variable spectroscopy element according to claim 1, wherein at least a part of the inclined surfaces, in the circumferential direction, is provided with areas without the wiring patterns and the connecting patterns.

5. A spectroscopy apparatus comprising a variable spectroscopy element according to claim 1; and
an image-acquisition device that captures light spectrally separated by the variable spectroscopy element.

6. An endoscope system comprising the spectroscopy apparatus according to claim 5.

* * * * *